(12) United States Patent
Okanobori et al.

(10) Patent No.: US 7,288,502 B2
(45) Date of Patent: Oct. 30, 2007

(54) CATALYST PARTICLE USABLE FOR DEHYDROGENATION OF ALCOHOLS

(75) Inventors: Hitoshi Okanobori, Saitama-ken (JP); Atsushi Kamachi, Saitama-ken (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 506 days.

(21) Appl. No.: 10/647,431

(22) Filed: Aug. 26, 2003

(65) Prior Publication Data

US 2004/0133045 A1 Jul. 8, 2004

(30) Foreign Application Priority Data

Aug. 27, 2002 (JP) ............................. 2002-247640

(51) Int. Cl.
 *B01J 21/18* (2006.01)
 *B01J 23/40* (2006.01)
 *B01J 23/74* (2006.01)
(52) U.S. Cl. .................................................. 502/185
(58) Field of Classification Search ................. 502/185
 See application file for complete search history.

(56) References Cited

U.S. PATENT DOCUMENTS

| | | | | |
|---|---|---|---|---|
| 5,569,635 A | * | 10/1996 | Moy et al. | ................... 502/185 |
| 5,874,166 A | * | 2/1999 | Chu et al. | ................... 428/368 |
| 6,432,866 B1 | * | 8/2002 | Tennent et al. | ............. 502/180 |
| 6,485,858 B1 | * | 11/2002 | Baker et al. | .................. 429/40 |
| 6,706,658 B2 | * | 3/2004 | White | ......................... 502/182 |
| 6,746,597 B2 | * | 6/2004 | Zhou et al. | .................. 208/138 |
| 6,753,290 B1 | * | 6/2004 | Romanenko et al. | ....... 502/185 |
| 6,800,584 B2 | * | 10/2004 | Baker et al. | ................. 502/184 |
| 6,841,509 B1 | * | 1/2005 | Hwang et al. | .............. 502/180 |

FOREIGN PATENT DOCUMENTS

JP 62-079289 * 11/1987

OTHER PUBLICATIONS

Likholobov, V.A., et al. "New Carbon-Carbonaceous Composites for Catalysis and Adsorption", Sep. 1994, React. Kinet. Catal. Lett. vol. 54, No. 2, pp. 381-411, (1995).*

* cited by examiner

*Primary Examiner*—J. A. Lorengo
*Assistant Examiner*—Patricia L. Hailey
(74) *Attorney, Agent, or Firm*—Arent Fox, LLP

(57) ABSTRACT

A catalyst particle containing an active metal and a carrier composed of a carbon material, wherein the active metal being supported by cavities on a surface of the carrier and their edge portions. The active metal is fixedly attached to the carrier for a long period of time, so that the catalyst particle stably shows a high catalytic activity, which is hardly reduced by a reaction. The catalyst particle is usable for the dehydrogenation of alcohols.

5 Claims, 13 Drawing Sheets

Mesophase Carbon

Carbon Black

Common Activated Carbon

Cup-Stacked-Type Carbon

Fig. 1(a)

Mesophase Carbon

Fig. 1(b)

Common Activated Carbon

Fig. 1(c)

Carbon Black

Fig. 1(d)

Cup-Stacked-Type Carbon

CATALYST PARTICLE USABLE FOR DEHYDROGENATION OF ALCOHOLS

FIELD OF THE INVENTION

The present invention relates to a catalyst particle comprising an active metal supported by a carrier composed of a carbon material, and particularly to a high-performance catalyst particle for dehydrogenating alcohols to produce hydrogen with high, stable activity, which suffers from little decrease with the reaction time, and a catalyst particle usable in electrodes of thermally regenerative fuel cells and polymer electrolyte fuel cells.

BACKGROUND OF THE INVENTION

Chemical heat pumps are energy-saving technologies utilizing reversible, exothermic and endothermic reactions of alcohols, etc. to efficiently convert a lower-grade heat to a value-added higher-grade heat, which can be used for heating, carburation, chemical thermal storage, etc. Thermally regenerative fuel cells can use working substances repeatedly in reaction systems with lower-grade thermal energy as a heat source, to efficiently convert free energy changes in chemical reactions to electric energy.

A catalyst for dehydrogenating 2-propanol as a working substance to acetone is described in JP 61-72995 A. In chemical heat pumps using this acetone/hydrogen/2-propanol system, it is important to dehydrogenate 2-propanol rapidly at a low temperature. The most important is, thus, to improve a dehydrogenation catalyst for converting 2-propanol to acetone. Proposed as improved dehydrogenation catalysts for the chemical heat pumps are Ru—, Rh—, or Pt-based catalysts described in JP 3-263550 A, Ru/Pt-based catalysts described in JP 4-98054 A, etc. Though the dehydrogenation catalysts of active metals such as Ru, Rh and Pt are disclosed in these references, carriers composed of carbon materials for supporting the active metals are not described. A carrier composed of silicon oxide is proposed in JP 9-178294 A as a catalyst carrier for chemical heat pumps using a methanol/methyl formate/hydrogen system. However, even though the active metals have excellent catalytic activity, it is difficult to fix the dispersed active metals to the silicon oxide carrier for a long period of time. Thus, catalyst particles with this carrier are disadvantageously unstable, degrading as the reaction time goes.

OBJECT OF THE INVENTION

Accordingly, an object of the present invention is to provide a catalyst particle comprising an active metal supported firmly by a carrier composed of a carbon material, which stably shows an excellent catalytic activity for a long period of time without substantial deterioration and thus is usable for high-efficient dehydrogenation of alcohols.

SUMMARY OF THE INVENTION

As a result of intense research in view of the above object, the inventors have found that a catalyst particle comprising a carbon carrier and an active metal supported by cavities on a carrier surface and their edge portions can stably maintain high catalytic activity for a long period of time without substantial deterioration, thus usable not only as a dehydrogenation catalyst but also as a fuel cell electrode catalyst, etc. The present invention has been completed based on this finding.

Thus, the catalyst particle of the present invention comprises an active metal and a carrier composed of a carbon material, the active metal being supported by cavities on a carrier surface and their edge portions.

The carbon carrier is preferably a mesophase carbon, an activated carbon having a high cavity density and a large surface area, or at least one selected from the group consisting of cup-stacked-type carbon, carbon nanotubes, carbon nanofibers and carbon nanohorns.

The cavities preferably have an average diameter of 0.5 to 5 nm. The active metal is preferably Ru, Pt or an alloy thereof. Further, the catalyst particle of the present invention is preferably used for the dehydrogenation of alcohols.

DETAILED DESCRIPTION OF THE PREFERRED EMBODIMENTS

[1] Catalyst Particle

The catalyst particle of the present invention comprises an active metal and a carrier composed of a carbon material. Cavities are formed on a surface of the carrier, and the active metal is supported by cavities and their edge portions.

(1) Carbon Carrier

The carbon carrier having cavities defined by their edge portions on its surface is typically composed of a mesophase carbon, a cup-stacked-type carbon, etc. FIGS. 1(a) to 1(d) show various carbon materials supporting the active metal. In a case where a certain amount of an active metal 2 such as Ru is supported by a carrier 1 with surface cavities such as a mesophase carbon shown in FIG. 1(a) and a cup-stacked-type carbon shown in FIG. 1(d), the resultant catalyst particle is higher in activity for the dehydrogenation of alcohols, etc., than a catalyst particle using a carrier without cavities such as carbon black shown in FIG. 1(c). The active metal 2 is fixedly attached to the cavities of the carrier 1 of the mesophase carbon, etc., and this is different from a case where the active metal is supported by a carbon black carrier, etc. with a small contact area. When the active metal is fixedly attached to the cavities, the active metal shows a high reaction activity and is free from deterioration like so-called sintering, by which the active metal moves and agglomerates on the carrier.

Figure 1A:
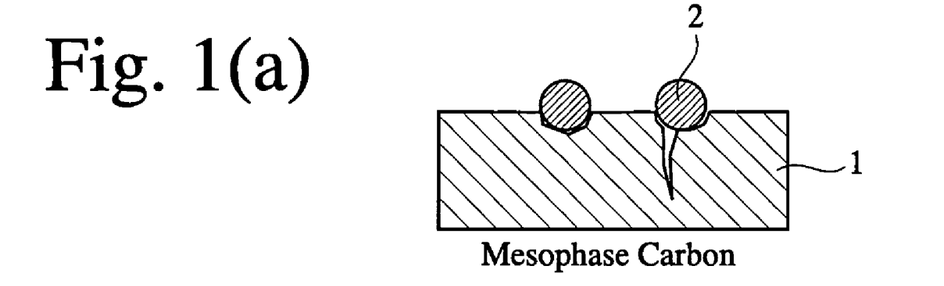
FIGS. 1(a) to 1(d) are schematic cross-sectional views showing various carbon materials supporting an active metal.
Figure 1B:
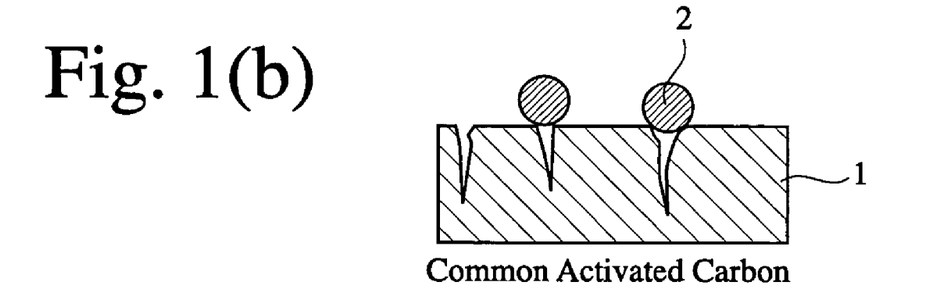
Figure 1C:
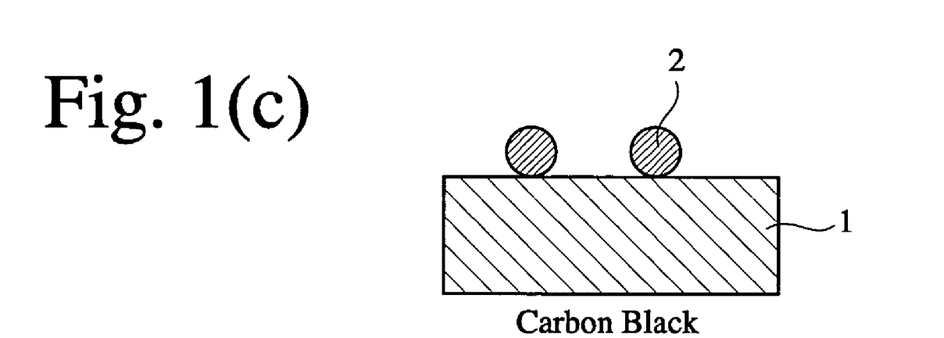
Figure 1D:
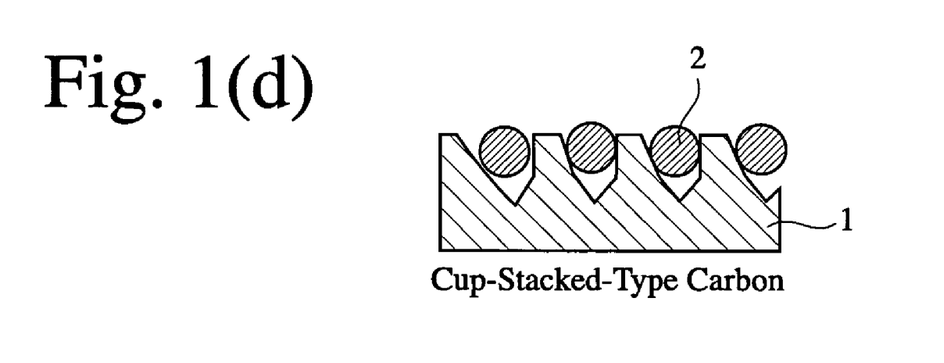
Figure 2:
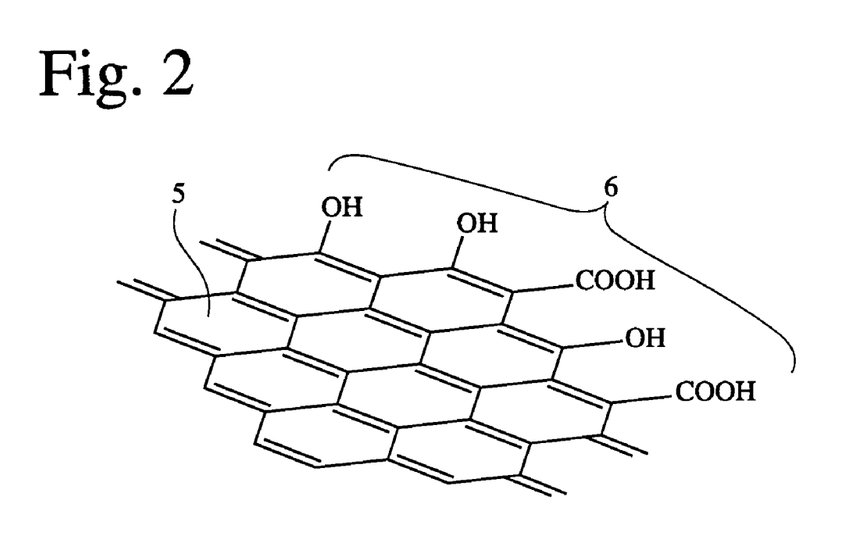
FIG. 2 is a schematic view showing a crystal structure of a mesophase carbon.

The mesophase carbons have the same crystal structure as that of graphite. FIG. 2 shows a crystal structure of a mesophase carbon comprising a basal plane 5 having a cyclic structure and an edge 6 having functional groups such as —OH and —COOH. The mesophase carbons are composed of oriented crystallites having such a crystal structure as shown in FIG. 2. It is considered that because of the functional groups, the edge 6 and its vicinity, which are called "edge portion," have a larger bonding force to the active metal than the basal plane 5.

The carrier composed of a mesophase carbon may be prepared by activating easily graphitizable carbon such as a mesophase pitch. Specifically, the carrier may be prepared by the steps of subjecting a mesophase pitch to an infusibilization treatment and a carbonization treatment to obtain carbonized powder; sufficiently mixing the carbonized powder with an activator comprising KOH pellets and NaOH pellets; heating the resultant mixture at 800° C. to 1000° C. for 2 to 5 hours; and removing KOH and NaOH from the treated powder.

Figure 3:
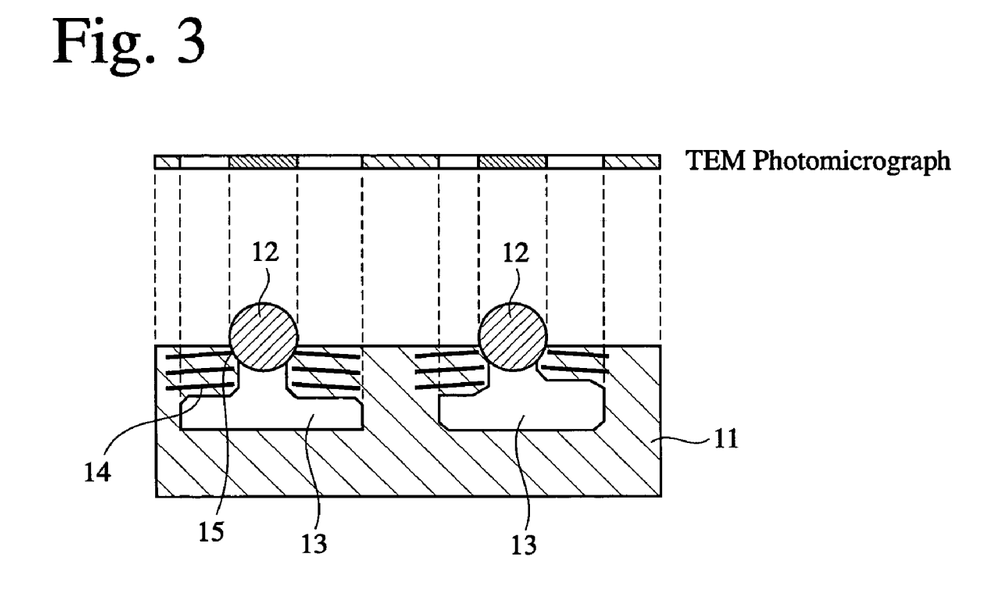
FIG. 3 is a schematic cross-sectional view showing an active metal supported by a carrier composed of a mesophase carbon.
Figure 4:
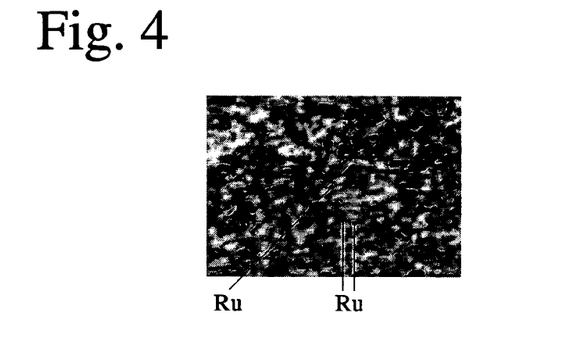
FIG. 4 is a transmission electron photomicrograph (TEM photomicrograph) showing an active metal supported by a carrier composed of a mesophase carbon.

FIG. 3 schematically shows an active metal supported by a carrier composed of a mesophase carbon. The active metal 12 is adsorbed onto an edge portion 15 of the carrier 11 and supported by a cavity 13. FIG. 4 is a transmission electron photomicrograph (TEM photomicrograph) of 300,000 magnifications showing the active metal supported by the carrier composed of the mesophase carbon. As shown in FIG. 3, the active metal particles 12 are the darkest, the cavities are white, and the carrier has an intermediate brightness in the TEM photomicrograph. It is clear from the TEM photomicrograph of FIG. 4 that the active metal (Ru) is supported by the carrier of the mesophase carbon such that it enters into the cavities. Because the active metal particles are well dispersed, the catalyst particle has a large active metal surface area and thus high reaction activity.

On the contrary, in the case of using a carrier made of carbon black usually having a bead-chain structure, cavities on the carbon black carrier are too large to fixedly support an active metal thereon. Carriers with deep cavities between carbon particles are not preferable because a reactive substance such as alcohol molecules hardly penetrates into such deep cavities. Common activated carbon particles are prepared from precursors by carbonization and activation treatments, by which internal cavities are formed in the precursors to increase their adsorption surface areas while reducing their weight. Thus, many smaller cavities are observed by TEM, etc. mainly inside the activated carbon particles. As a result, such activated carbon particles cannot stably fix the active metal particles in their cavities unlike the mesophase carbon.

The cavities preferably have such size as to permit reactive substances such as alcohols to easily penetrate thereinto while stably supporting the active metal. Thus, the average diameter of the cavities is preferably 0.5 to 5 nm, more preferably 2 to 5 nm. The carrier preferably has a specific surface area of 80 to 3000 $m^2/g$, and preferably has an average particle size of 0.01 to 10 μm.

Figure 5:
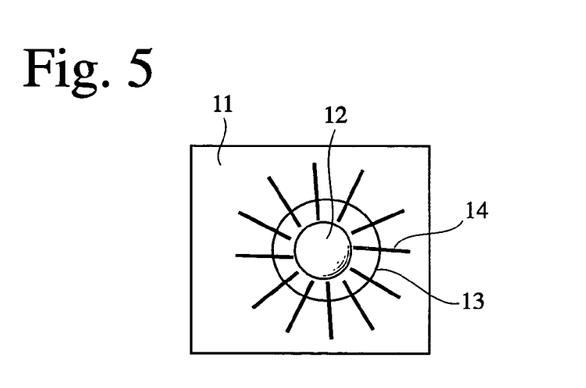
FIG. 5 is a schematic view showing an active metal supported by a carrier composed of a mesophase carbon.
Figure 6:
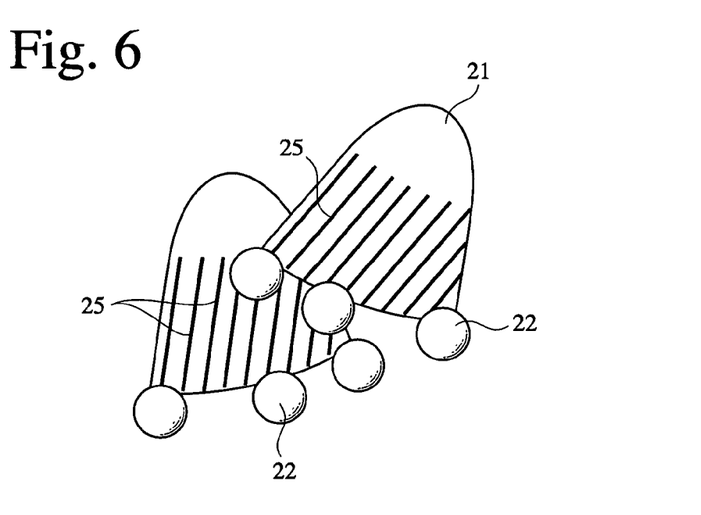
FIG. 6 is a schematic view showing an active metal supported by a carrier composed of a carbon nanohorn.
Figure 7:
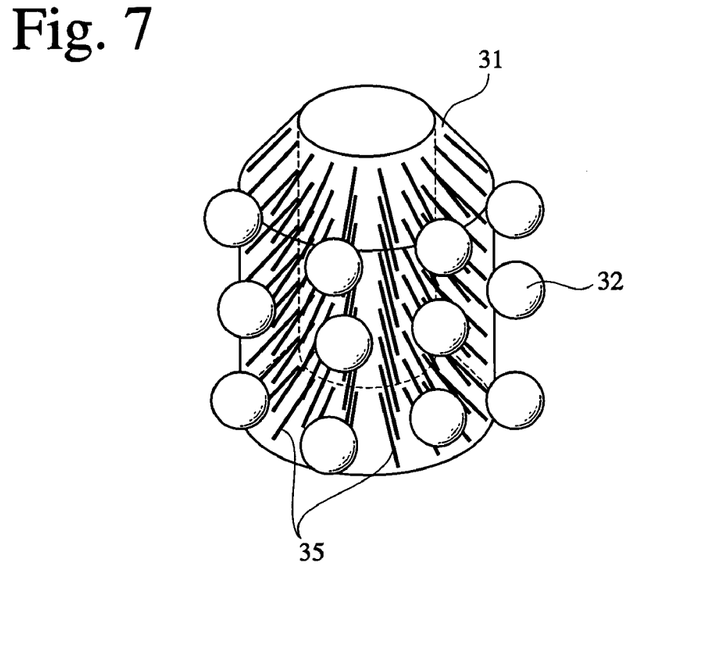
FIG. 7 is a schematic view showing an active metal supported by a carrier composed of a cup-stacked-type carbon.

Each of FIGS. 5 to 10 schematically shows how an active metal is adsorbed onto a carbon carrier. As shown in FIG. 5, mesophase carbon crystallites 14 are oriented toward a cavity 13, so that an active metal 12 is adsorbed onto the edge portion of the cavity 13 with a strong bonding force. Similarly, carriers composed of carbon nanohorns shown in FIG. 6, cup-stacked-type carbon shown in FIG. 7, or activated carbon shown in FIG. 10 having a high cavity density and a large surface area (specific surface area of 2000 to 3000 $m^2/g$) have a strong bonding force to active metals 22, 32, 62 in their edge portions because of the regularly oriented crystallites 25, 35, 65. On the contrary, carriers composed of carbon black such as furnace black and Ketjen black shown in FIG. 8 or activated carbon shown in FIG. 9 having a small surface area (specific surface area of 60 to 200 $m^2/g$) have a small bonding force to the active metal in their edge portions because of the irregularly oriented crystallites 45, 55. Therefore, an active metal cannot be fixedly attached to the carbon particle surfaces for a long period of time, resulting in gradual detachment of the active metal. Further, agglomeration (sintering) occurs on the surfaces of carbon particles and activated carbon by the movement of the active metal particles by catalytic reaction, so that the active metal surface, namely a catalytically active surface, has a reduced area, resulting in decreased reactivity.

When the active metal is supported by the carbon carrier, it is presumed that the active metal is first supported by the cavities by the adsorption effect of their edge portions, and then firmly held by the cavities by their anchoring effect. Thus, in the catalyst particles of the present invention, the active metal is supported by the carrier by the synergy of the adsorption effect of the edge portions and the anchoring effect of the cavities for a long period of time. Accordingly, the active metal particles are dispersed on the carrier with suppressed agglomeration.

The carbon carrier for supporting the active metal may be in various forms. Examples of carbon materials as effective as the mesophase carbon are those having nanostructures such as cup-stacked-type carbon, carbon nanotubes, carbon nanofibers and carbon nanohorns. These carbon materials having cavities and edge portions on their surfaces exhibit an active metal-bonding effect (adsorption effect) and an active metal-fixing effect (anchoring effect), like the mesophase carbon. Therefore, such carbon materials provide (1) high dispersion, (2) high reaction activity, and (3) resistance to deterioration due to the agglomeration of the active metal.

Figure 11A:
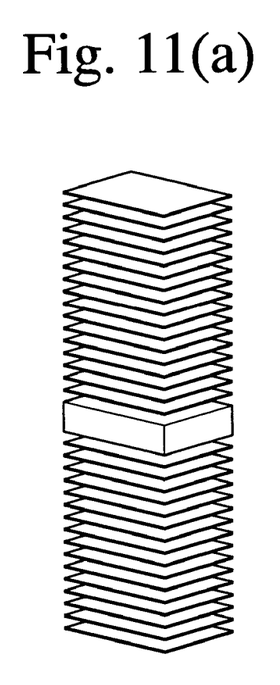
FIGS. 11(a) to 11(c) are schematic views showing the structures of various carbon nanofibers.
Figure 11B:
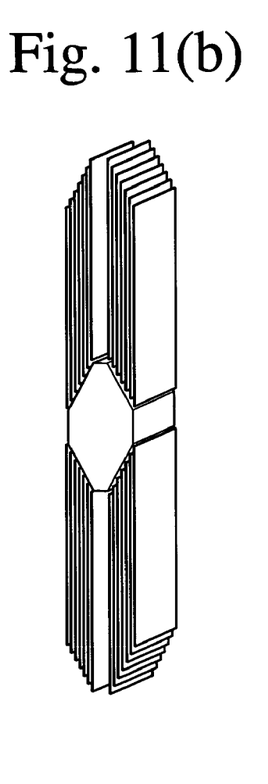
Figure 11C:
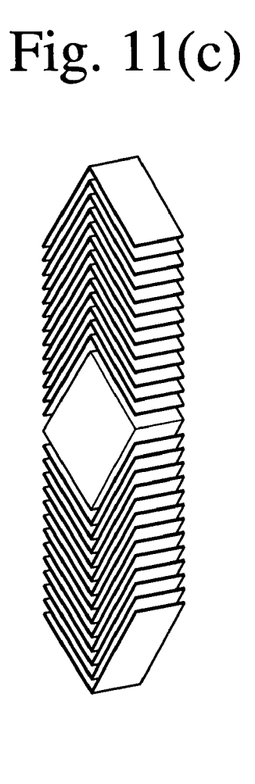

The structures and production methods of carbon nanotubes and carbon nanofibers are described in J. Phys. Chem. B 105(6) 1115-1118 (2001), National Institute for Resources and Environment, News of NIRE (1998), etc. The carbon nanotubes may have diameters of approximately 1 to 10 nm with a multi-walled nanotube structure with carbon walls formed around one nanotube. The carbon nanotubes may be prepared by an arc discharge using a carbon electrode, or by thermal decomposition of a hydrocarbon gas using a fine metal particle catalyst. The carbon nanohorns have a structure with carbon nanotubes, one end of which is closed. The carbon nanofibers have diameters of ten to several hundreds nm and lengths of a few micrometers. The carbon nanofibers may have a platelet-type structure shown in FIG. 11(a), in which carbon planes are oriented vertically to the fiber axis, a ribbon-type structure shown in FIG. 11(b), in which carbon planes are oriented parallel to the fiber axis, or a herringbone-type structure shown in FIG. 11(c), in which carbon planes are inclined against the fiber axis. The carbon nanofibers may be prepared by thermal decomposition of a carbon source gas using a metal catalyst such as iron and cobalt, in which the carbon source gas is a hydrocarbon such as ethylene, carbon monoxide, etc.

(2) Active Metal

The active metal may be selected from various metals and alloys depending on the desired catalytic reactions. Ru, Pt and their alloys are preferably used for the dehydrogenation of alcohols, showing excellent activity in the dehydrogenation of 2-propanol, methanol, ethanol, isobutyl alcohol, etc. The amount of the active metal in the catalyst particles may be controlled depending on the reactions, the kind of the metals, etc. The active metal is not restricted to a simple substance, but may be in the form of an oxide, etc. Thus, the amount of the active metal is expressed herein as the mass of a corresponding metal element.

(3) Production Method

Though the active metal may be disposed on the carrier by various methods, it is preferable to use a dry diffusion method, particularly a diffusion-adsorption method, because of simplicity and the use of commercially available catalysts such as Ru catalysts.

When a dehydrogenation catalyst carrying Ru as an active metal is produced by the dry diffusion method, for example, the carrier and the catalytic metal complex are weighed and completely mixed by a mixing apparatus such as a mortar and a ball mill, and the resultant mixture is put in an airtight container having a stirring means, heated at 120° C. for 1 hour in an $N_2$ flow while stirring, heated at 180° C. for 1 hour in an $H_2$ flow to reduce it, and then cooled to an ambient temperature in an $H_2$ flow; followed by $N_2$ purging.

(4) Properties and Applications

When the catalyst particles of the present invention may be used as a catalyst for the dehydrogenation of alcohols in chemical heat pumps, thermally regenerative fuel cells, etc, they have high hydrogen-generating activity with their active metal held for a long period of time, thereby showing stable catalytic activity.

[2] Chemical Heat Pump

Figure 12:
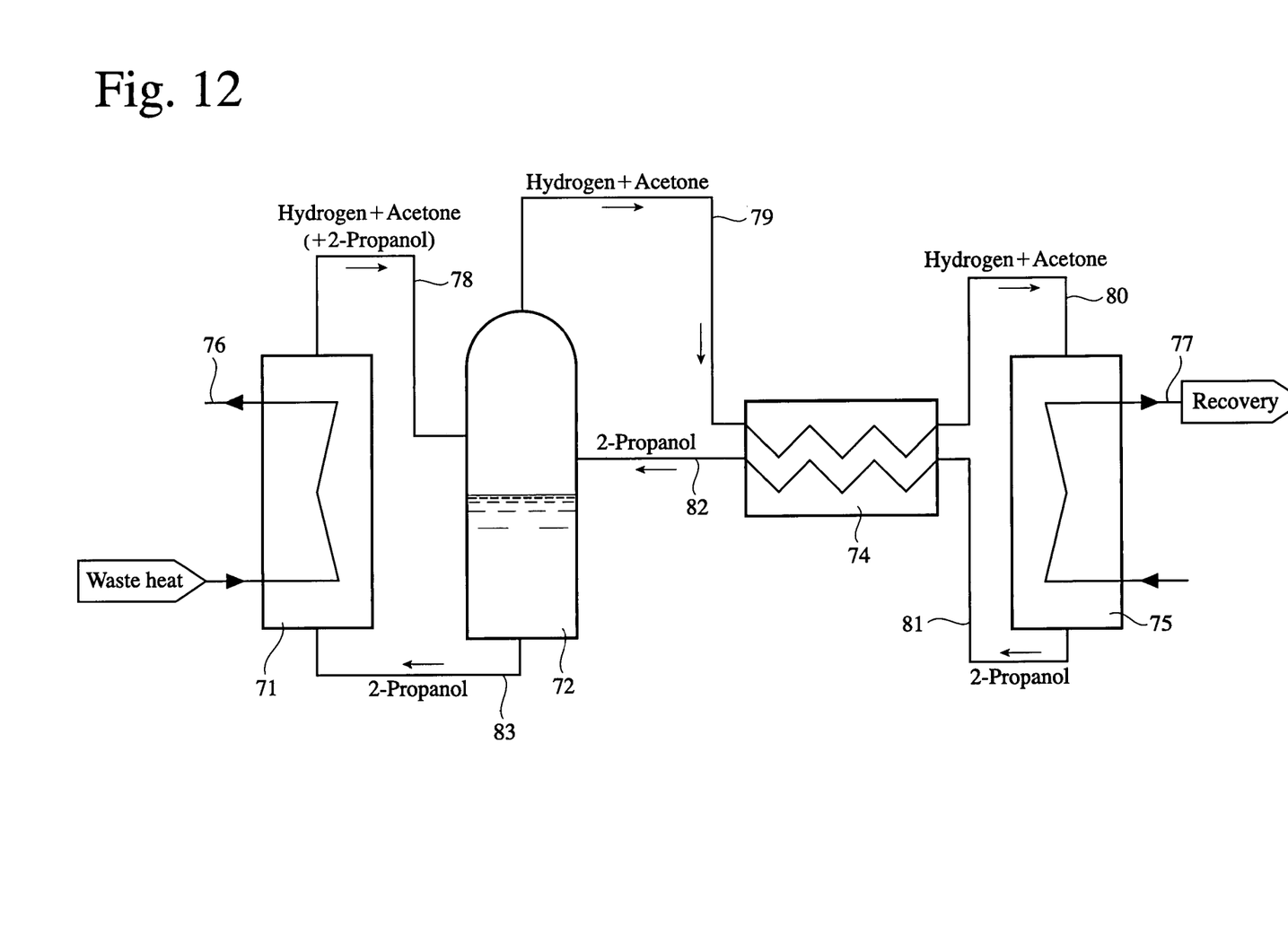
FIG. 12 is a schematic view showing a chemical heat pump using an acetone/hydrogen/2-propanol system.

The catalyst particle of the present invention may be used as a dehydrogenation catalyst for a chemical heat pump, which utilizes reversible, exothermic and endothermic reactions of a working substance of an alcohol to recover thermal energy from lower-grade heat such as natural heat (ground heat, solar heat, etc.) and industrial waste heat. A chemical heat pump utilizing an acetone/hydrogen/2-propanol system using 2-propanol as the working substance shown in FIG. 12 is described in detail below.

An endothermic reactor 71 for an endothermic reaction between hydrogen and acetone has a line 76, through which a heat medium is circulated to transfer heat from an external heat source (not shown). Hydrogen and acetone obtained by dehydrogenating 2-propanol are transported from the endothermic reactor 71 through a line 78, which is connected to a distillation column 72. The top of the distillation column 72 is connected to a heat exchanger 74 by a line 79.

A line 80 from the heat exchanger 74 is connected to an exothermic reactor 75. The exothermic reactor 75 has a line 77, and a heat medium is circulated through the line 77 to recover thermal energy from the reactor 75. The reaction product (2-propanol) is transported through a line 81 from the exothermic reactor 75 to the heat exchanger 74, cooled in the heat exchanger 74, transported through a line 82, and collected in the distillation column 72. A line 83 from the bottom of the distillation column 72 is connected to the endothermic reactor 71, so that 2-propanol is recovered and recycled as a starting material of the endothermic reaction.

(1) Endothermic Reactor

The endothermic reactor 71 comprises a reaction zone having a dehydrogenation catalyst layer and a heating zone, to convert 2-propanol to hydrogen and acetone. The catalyst particle comprising Ru supported by a mesophase carbon carrier may be used as the dehydrogenation catalyst. The dehydrogenation reaction is continued by heat from the external heat medium, which is circulated through the line 76 in the endothermic reactor 71. The reaction temperature is preferably 80 to 100° C. The heat medium cooled to 80° C. or lower by the endothermic reaction is recovered, heated by the external heat source, and used for the reaction repeatedly. The reaction mixture produced in the endothermic reactor 71 contains acetone, hydrogen and unreacted 2-propanol. The reaction mixture is transported to the distillation column 72 through the line 78.

(2) Distillation Column

In the distillation column 72, the reaction mixture is heated at 60 to 80° C. to separate hydrogen and acetone from the unreacted 2-propanol, utilizing the difference in a boiling point between 2-propanol (82.4° C.) and acetone (56.5° C.). The mixture of hydrogen and acetone is transported through the line 79 provided on the top of the distillation column 72, and the separated 2-propanol is transported to the endothermic reactor 71 through the line 83 connected to the bottom of the distillation column 72.

(3) Heat Exchanger

A counterflow-type heat exchanger, etc. may be used as a heat exchanger 74. The cooled hydrogen and acetone, and hot 2-propanol produced in the exothermic reactor 75 are counter-flowed in the heat exchanger 74 for heat exchange. The hydrogen and acetone are pre-heated in the heat exchanger 74, and transported to the exothermic reactor 75 through the line 80.

(4) Exothermic Reactor

The exothermic reactor 75 comprises a reaction zone having a hydrogenation catalyst layer and the line 77. The heat medium is circulated through the line 77 to recover the reaction heat produced in the exothermic reaction. The pre-heated hydrogen and acetone are transported into the exothermic reactor 75, and the acetone is hydrogenated to 2-propanol in the presence of the hydrogenation catalyst. Because the hydrogenation reaction is exothermic, higher-grade thermal energy can be recovered from the external lower-grade heat source. 2-Propanol produced by the hydrogenation is subjected to heat exchange with hydrogen and acetone in the heat exchanger 74. The 2-propanol is then transported to the endothermic reactor 71 through the distillation column 72, and dehydrogenated. Thus, 2-propanol is repeatedly used while circulating in the chemical heat pump.

[3] Thermally Regenerative Fuel Cell

Figure 13:
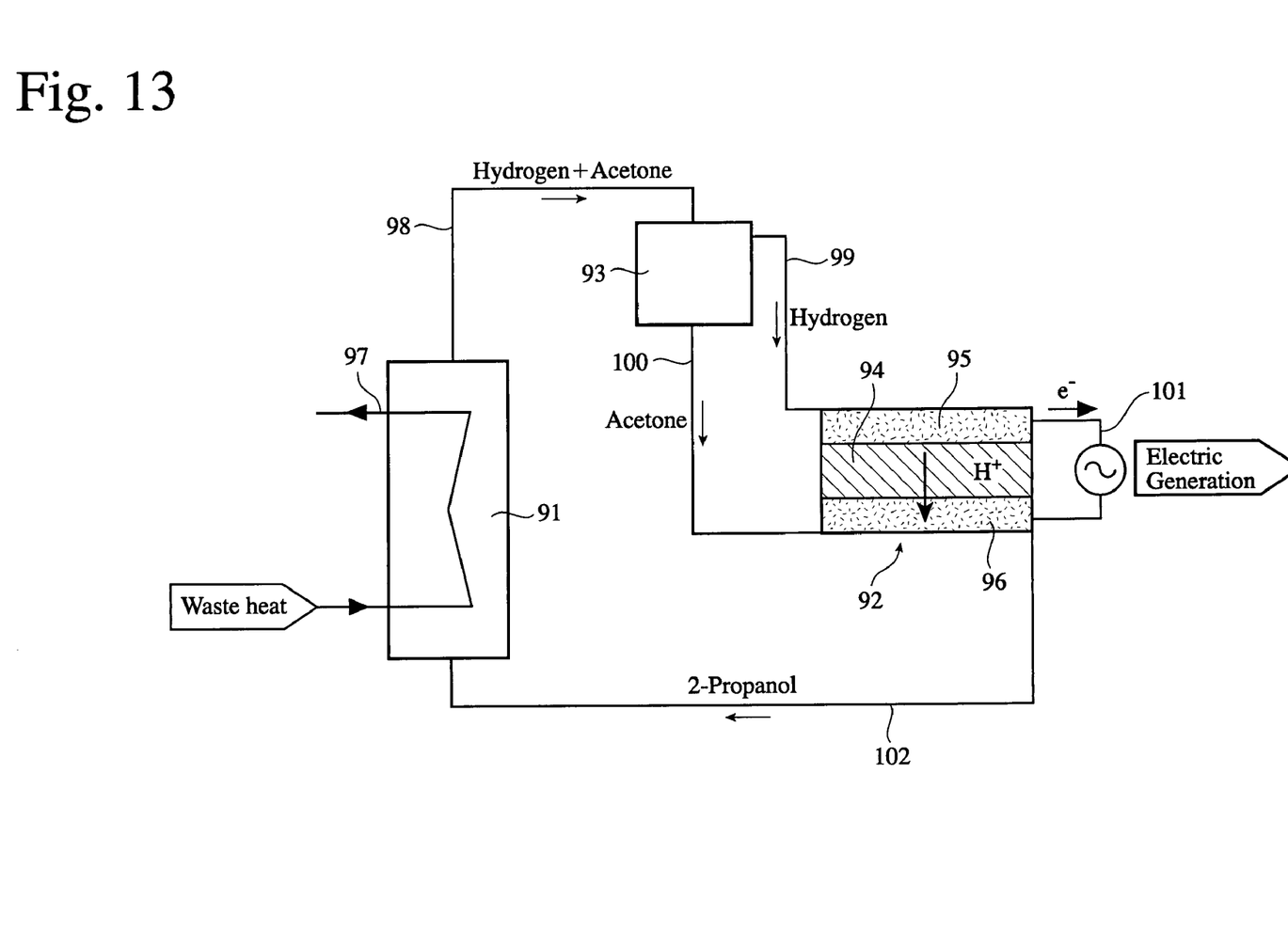
FIG. 13 is a schematic view showing a thermally regenerative fuel cell using an acetone/hydrogen/2-propanol system.

The catalyst particle of the present invention for dehydrogenation may be used in a thermally regenerative fuel cell, which uses a working substance repeatedly to convert chemical energy of a fuel such as a hydrogen gas directly to electric energy by electrochemical reactions. In particular, the catalyst particle is preferably used in a thermally regenerative fuel cell using an acetone/hydrogen/2-propanol system, and an example thereof is shown in FIG. 13.

A dehydrogenation reactor 91 has a line 97 for supplying a heat medium from an external heat source (not shown). The dehydrogenation reactor 91 is connected to a hydrogen/acetone separation apparatus 93 by a line 98 to transport the reaction products (hydrogen and acetone). A line 99 for transporting the hydrogen separated in the separation apparatus 93 is connected to a negative electrode 95 of a power-generating means 92. On the other hand, a line 100 for transporting the separated acetone is connected to a positive electrode 96 of the power-generating means 92. Electrons $e^-$ generated in the negative electrode 95 are extracted as electric energy in an external circuit 101. Protons $H^+$ produced in the negative electrode 95 pass through a polymer electrolyte film 94, and react with acetone and electrons provided from the external circuit 101 in the positive electrode 96 to produce 2-propanol. The power-generating means 92 is connected to the dehydrogenation reactor 91 by a line 102, and the 2-propanol produced in the power-generating means 92 is circulated through the line 102 and recycled. The dehydrogenation reactor 91 of the thermally regenerative fuel cell may be basically the same as the endothermic reactor 71 of the chemical heat pump, so that the description of the dehydrogenation reactor 91 per se is omitted.

The power-generating means 92 comprises a plurality of cell units stacked via separators, and each cell unit comprises a couple of electrodes (a positive electrode 96 and a negative electrode 95) and a polymer electrolyte film 94 disposed between the electrodes. The polymer electrolyte film 94 is composed of a proton-exchange resin (ion-exchange resin). Examples of such ion-exchange resins include sulfonated perfluorocarbon resins, and sulfonated resins free from fluorine such as sulfonated polyetheretherketone (PEEK) resins and sulfonated polyethersulfone resins.

Each electrode 95, 96 comprises a diffusion layer and a catalyst layer. The diffusion layer transports electrons between the catalyst layer and the separator, and diffuses hydrogen and acetone and supplies them to the catalyst layer. Thus, the diffusion layer is electroconductive and porous. Specifically, the diffusion layer may be made of a carbon paper, a carbon cloth, a carbon felt, etc. The catalyst layer may be prepared by uniformly dispersing catalyst particles having platinum powder, etc. supported by carbon black particles in an organic solution of an ion-conductive binder; and applying the resulting slurry to the diffusion layer.

The separated hydrogen is transported to the negative electrode 95 of the power-generating means 92, and thus the reaction of $H_2 \rightarrow 2H^+ + 2e^-$ proceeds on the negative electrode 95 to produce protons ($H^+$) and electrons ($e^-$). The produced protons ($H^+$) pass through the polymer electrolyte film 94, and the electrons are recovered as electric energy in the external circuit 101. In the positive electrode 96, acetone, protons from the polymer electrolyte film 94, and electrons from the external circuit 101 are reacted to produce 2-propanol (acetone+$H^+$+$e^- \rightarrow$ 2-propanol). 2-Propanol thus produced is returned to the dehydrogenation reactor 91 and repeatedly circulated in the fuel cell.

[4] Polymer Electrolyte Fuel Cell

The catalyst particle of the present invention may be used in a polymer electrolyte fuel cell. For example, a cell unit of the polymer electrolyte fuel cell may comprise a polymer electrolyte film, an air electrode and a fuel electrode, an ion-exchange polymer used as a binder for making both electrodes proton-conductive, the catalyst particles of the present invention, and polytetrafluoroethylene (PTFE) particles. The PTFE particles are water-repellent to control the water retention of the air electrode and the fuel electrode. The polymer electrolyte fuel cell generally comprises a plurality of the cell units stacked via separators.

The present invention will be explained in more detail referring to Examples below without intention of restricting the present invention thereto.

EXAMPLE 1

(1) Preparation of Carrier Composed of Mesophase Carbon
(a) Preparation of easily graphitizable carbon powder A granular mesophase pitch was infusibilized at 320° C. for 10 minutes in airflow, and carbonized at 700° C. for 1 hour in a nitrogen flow, to obtain a carbonized powder. The carbonized powder was subjected to a grinding treatment to control its particle size, to prepare carbon powder having a density of 1.55 g/ml.

(b) Alkali activation treatment 2.5 g of the resultant carbon powder and 5.0 g of an activator comprising KOH pellets and NaOH pellets were put in a mortar and sufficiently mixed while grinding, and the resultant mixture was charged into an Inconel boat. The boat was placed in a tubular furnace, heated to 800° C. at a heating rate of 200° C./hour in a nitrogen flow of 60 ml/minute, and kept at that temperature for 2 hours. The boat was then taken out of the tubular furnace, and the mixture was subjected to ultrasonic washing with pure water for 15 minutes to remove KOH. The resultant mixture was washed with hydrochloric acid to remove NaOH, washed with approximately 3 L of warm water, filtered, and dried, to prepare a mesophase carbon carrier.

(2) Preparation of Catalyst Particle

A Ru-carbonyl complex was added to the above carrier and completely mixed in a mortar such that the ratio of Ru to the entire catalyst particles was 20% by mass. The resultant mixture was placed in a Schlenk tube, heated at 120° C. for 1 hour while stirring the mixture by a stirrer in an $N_2$ flow, and heated to 180° C. in an $H_2$ flow and reduced for 1 hour. Catalyst particles thus obtained were cooled to an ambient temperature in an $H_2$ flow, the Schlenk tube was purged by $N_2$, and the catalyst particles were enclosed in a sample tube in an $N_2$ flow.

Figure 14:
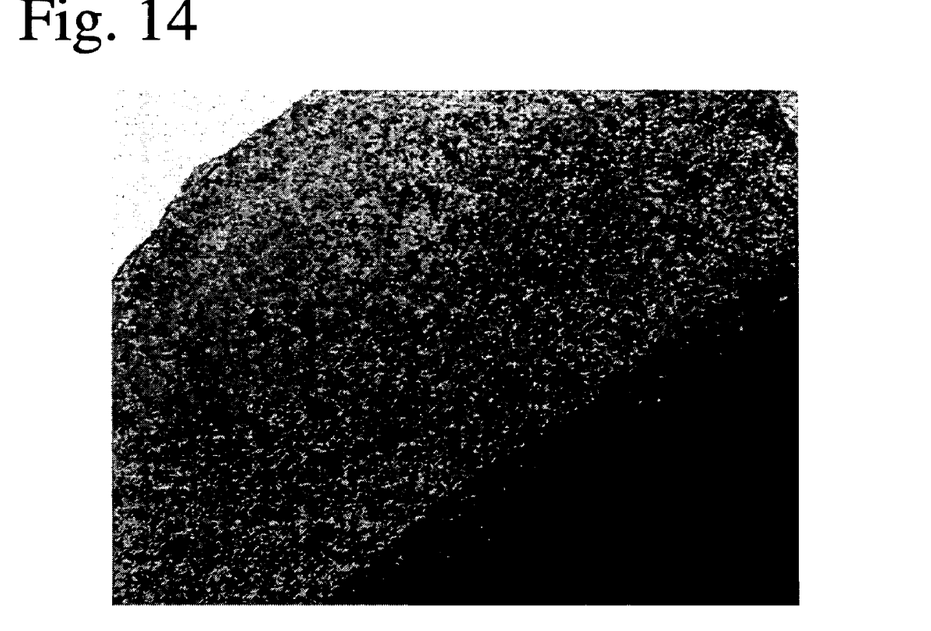
FIG. 14 is a transmission electron photomicrograph (TEM photomicrograph) showing the catalyst particle produced in Example 1.
Figure 15:
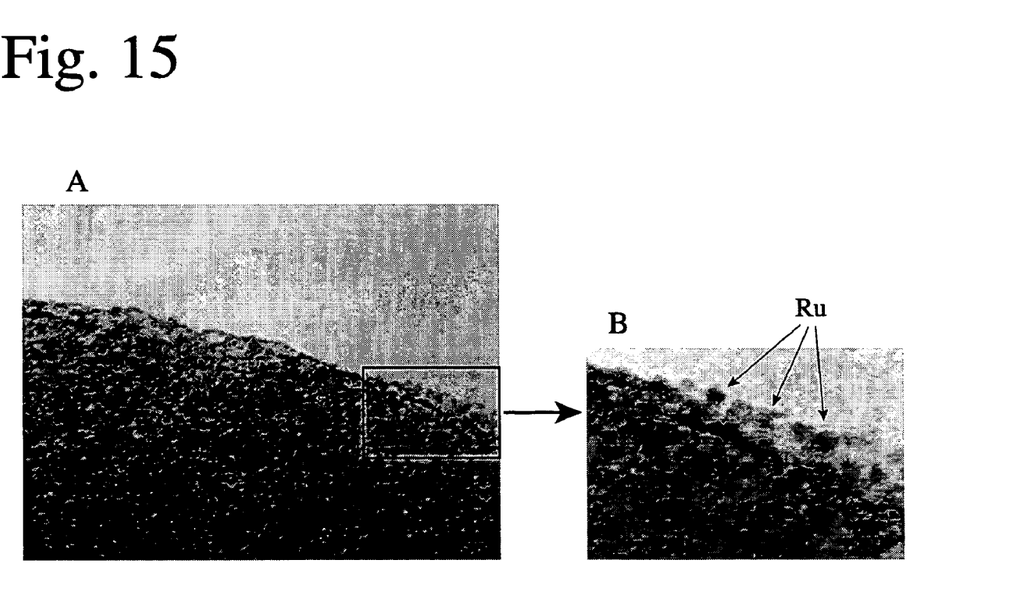
FIG. 15 is a transmission electron photomicrograph (TEM photomicrograph) showing a section of the catalyst particle produced in Example 1.

FIGS. 14 and 15 are TEM photomicrographs of 200,000 magnifications showing the catalyst particles. As is clear from the TEM photomicrograph of FIG. 14 and the TEM photomicrograph A of FIG. 15, innumerable cavities were formed on the surface of the mesophase carbon carrier. Further, it is clear from a TEM photomicrograph B, which is a partially enlarged photomicrograph of the TEM photomicrograph A, that the Ru particles were regularly arranged on the outer surface of the mesophase carbon carrier.

(3) Reactor

Figure 16:
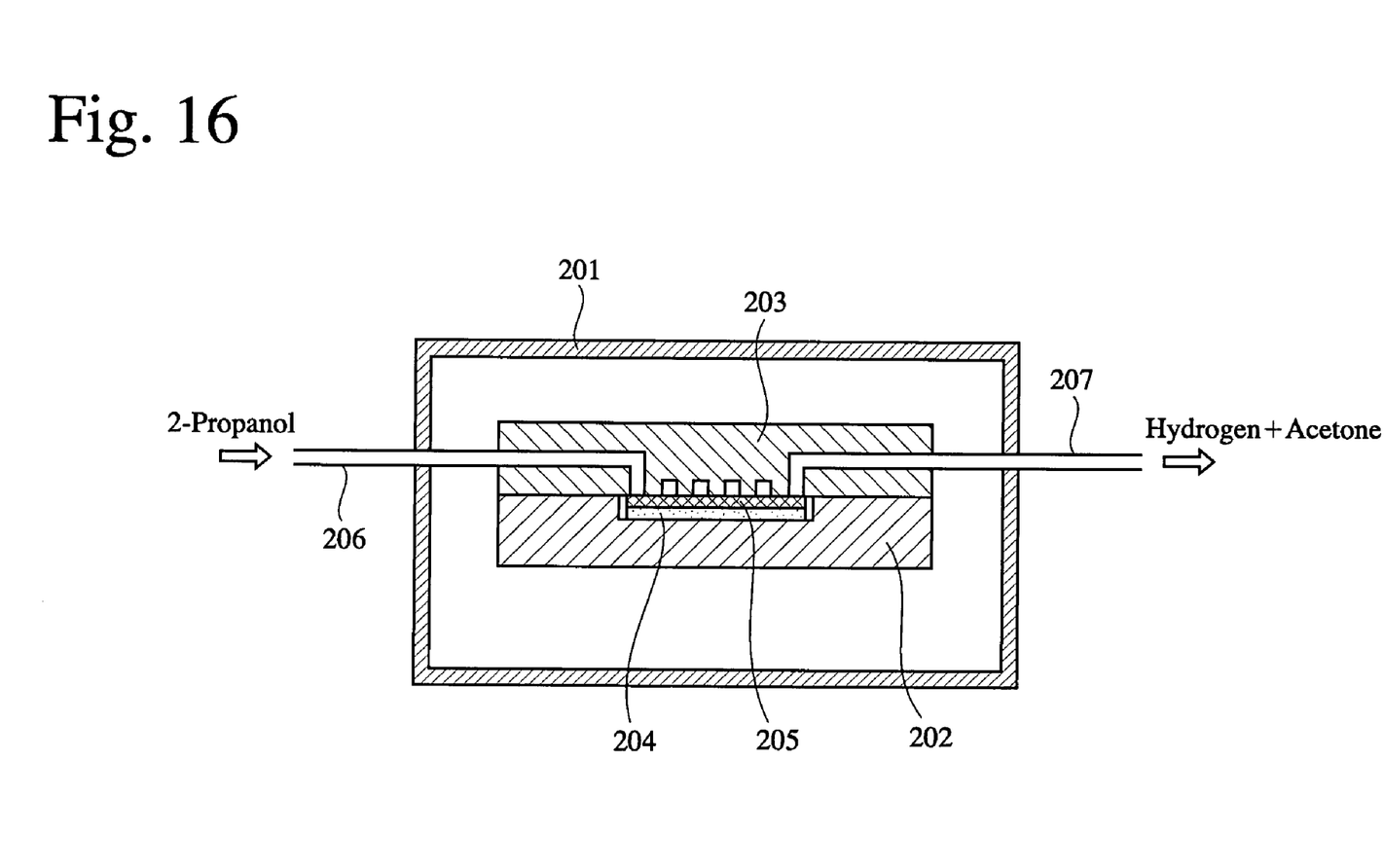
FIG. 16 is a schematic view showing a reactor for a dehydrogenation reaction test.
Figure 17A:
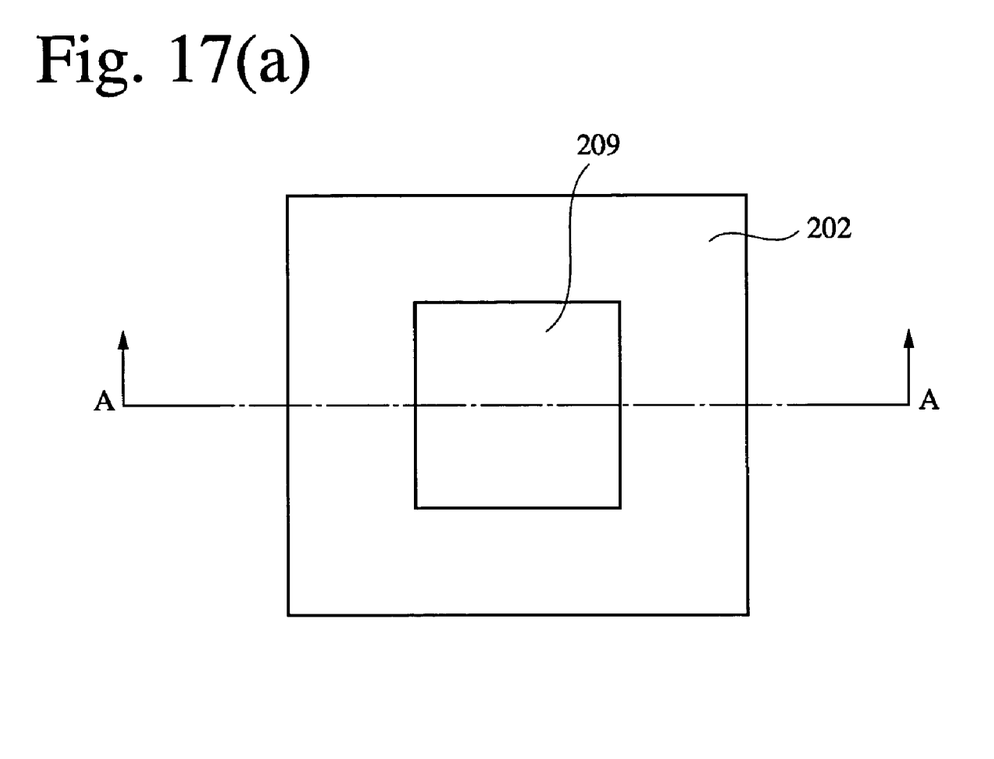
FIG. 17(a) is a top view showing a plate having a depression in which a catalyst is placed.
Figure 17B:
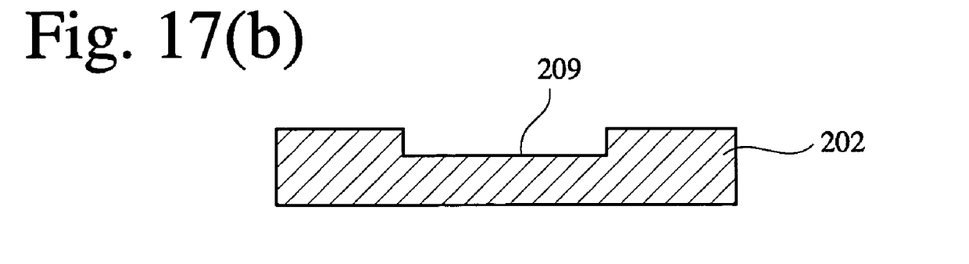
FIG. 17(b) is a cross-sectional view taken along the line A-A in FIG. 17(a)
Figure 18A:
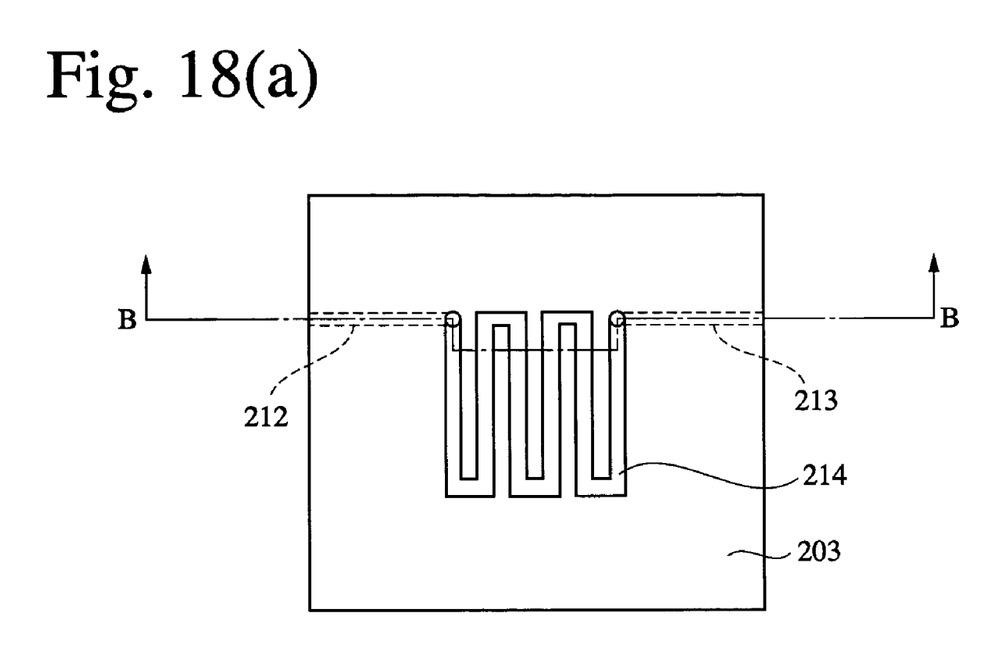
FIG. 18(a) is a bottom view showing a plate having a meandering groove.
Figure 18B:
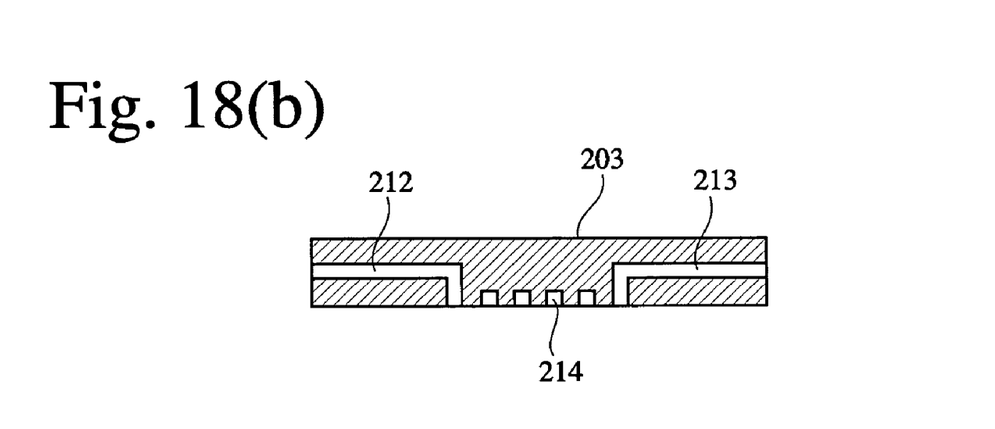
FIG. 18(b) is a cross-sectional view taken along the line B-B in FIG. 18(a)

A reactor shown in FIGS. 16 to 18 was used to evaluate the catalytic activity of the catalyst particles. The reactor comprised plates 202 and 203 placed in a thermostatic chamber 201, a pipe 206 for supplying 2-propanol, and a pipe 207 for removing acetone and hydrogen. As shown in FIGS. 17(*a*) and 17(*b*), the plate 202 had a recess 209 of 30 mm×30 mm×500 μm at a center for receiving the catalyst particles. A meandering groove 214 was formed on the bottom of the plate 203 at a position corresponding to the depression 209 of the plate 202. Ends of the meandering groove 214 were connected to pores 212 and 213, respectively. The pores 212 and 213 were connected to the pipes 206 and 207, respectively.

(4) Evaluation of Catalytic Activity

Figure 19:
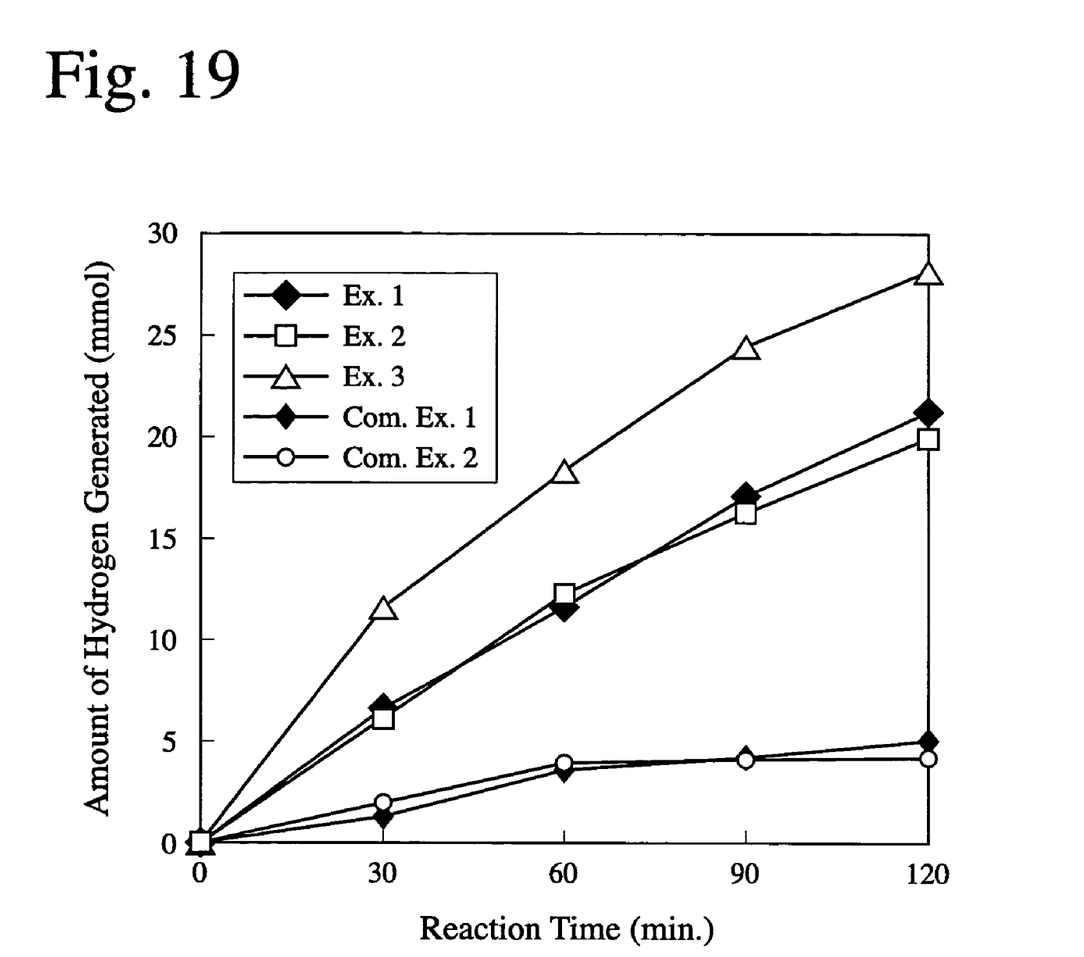
FIG. 19 is a graph showing the changes of hydrogen production by various catalyst particles comprising 20% by mass of Ru with the reaction time.

The Ru-mesophase carbon catalyst particles 204 produced above were attached to a carbon paper 205, and placed in the recess 209 of the plate 202. The plate 202 was covered with the plate 203, and the plates 202 and 203 were fixed by screws to seal the catalyst particles 204. 2-Propanol was supplied from the pipe 206 to the catalyst particles 204 for 120 minutes at a rate of 0.1 ml/minute while keeping the internal temperature of the thermostatic chamber 201 at 90° C. Hydrogen and acetone generated by the gas phase reaction was removed from the pipe 207. After acetone was separated, the amount of hydrogen produced was measured. The changes of the amount of hydrogen produced with the reaction time are shown in Table 1 and FIG. 19. The catalyst particles of Example 1 according to the present invention had a stable, high catalytic activity, which was hardly reduced with the reaction time.

EXAMPLE 2

Catalyst particles were produced and evaluated with respect to the catalytic activity in the same manner as in Example 1 except for using carbon nanohorns instead of the mesophase carbon for the carrier. The changes of the amount of hydrogen produced with the reaction time are shown in Table 1 and FIG. 19. The catalyst particles of Example 2 according to the present invention had a stable, high catalytic activity, which was hardly reduced with the reaction time. Incidentally, the carbon nanohorns used herein were those prepared by attaching a graphite electrode to a welding machine, subjecting the graphite electrode to arc discharge to produce soot, and rapidly cooling the soot by contact with a stainless steel plate.

EXAMPLE 3

Figure 10:
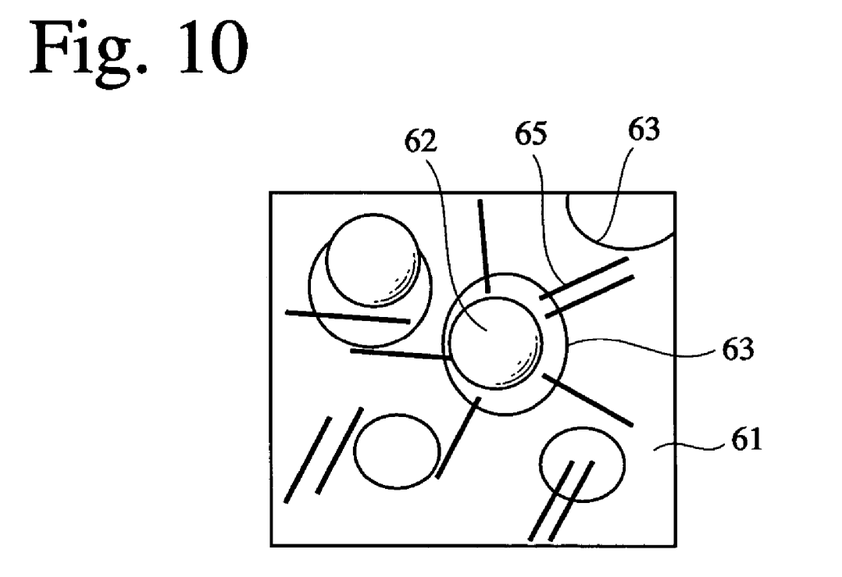
FIG. 10 is a schematic view showing an active metal supported by a carrier composed of an activated carbon having a large surface area.

Catalyst particles were produced and evaluated with respect to the catalytic activity in the same manner as in Example 1 except for using the activated carbon shown in FIG. 10 having a high cavity density and a large surface area (MSC30 available from Kansai Coke and Chemicals Co., Ltd. having a specific surface area of 2400 $m^2/g$) instead of the mesophase carbon for the carrier. The changes of the amount of hydrogen produced with the reaction time are shown in Table 1 and FIG. 19. The catalyst particles of Example 3 according to the present invention had a stable, high catalytic activity, which was hardly reduced with the reaction time.

COMPARATIVE EXAMPLE 1

Figure 8:
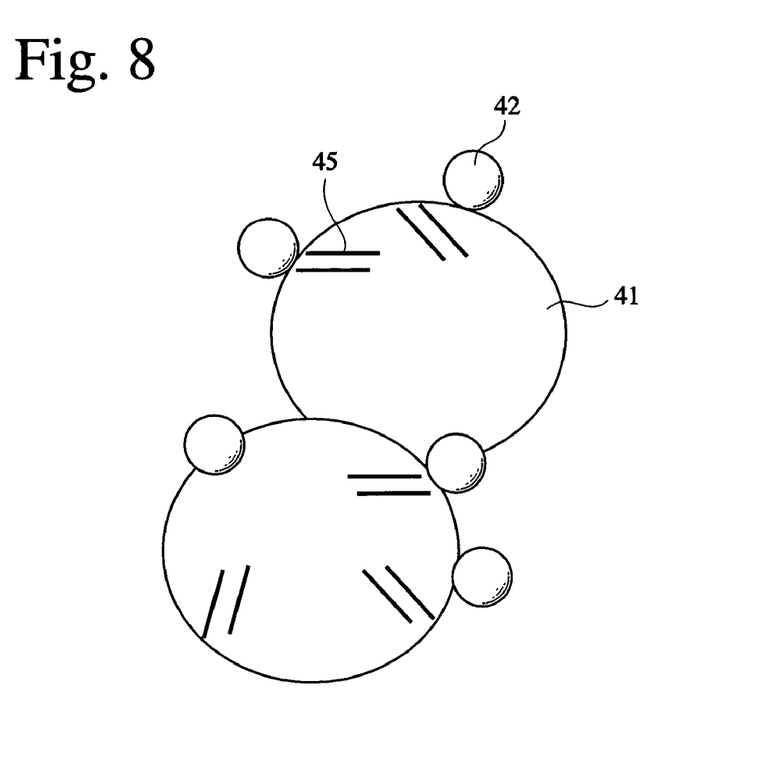
FIG. 8 is a schematic view showing an active metal supported by a carrier composed of carbon black.

Catalyst particles were produced and evaluated with respect to the catalytic activity in the same manner as in Example 1 except for using the carbon black shown in FIG. 8 (Denka Black HS-100 available from Denki Kagaku Kogyo Kabushiki Kaisha) instead of the mesophase carbon for the carrier. The changes of the amount of hydrogen produced with the reaction time are shown in Table 1 and FIG. 19. The catalyst particles of Comparative Example 1 showed remarkably lower catalytic activity than those of the catalyst particles of Examples 1 to 3.

COMPARATIVE EXAMPLE 2

Figure 9:
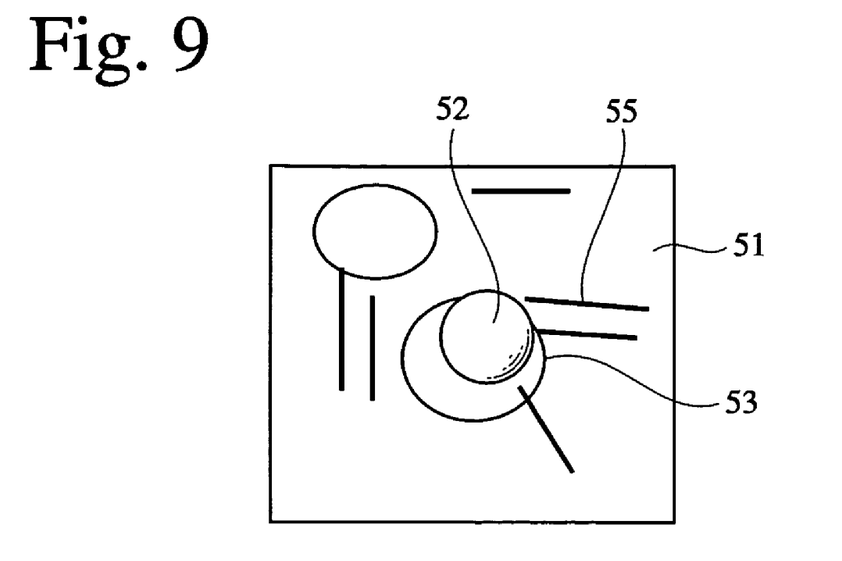
FIG. 9 is a schematic view showing an active metal supported by a carrier composed of an activated carbon having a small surface area.

Catalyst particles were produced and evaluated with respect to the catalytic activity in the same manner as in Example 1 except for using the activated carbon shown in FIG. 9 having a low cavity density and small surface area (Kuraraycoal GG available from Kuraray Chemical Co., Ltd. having a specific surface area of 120 $m^2/g$) instead of the mesophase carbon for the carrier. The changes of the amount of hydrogen produced with the reaction time are shown in Table 1 and FIG. 19. The catalyst particles of Comparative Example 2 showed remarkably lower catalytic activity than those of the catalyst particles of Examples 1 to 3.

TABLE 1

| Reaction time (minute) | Example 1 | Example 2 | Example 3 | Comparative Example 1 | Comparative Example 2 |
| --- | --- | --- | --- | --- | --- |
| 0 | 0 | 0 | 0 | 0 | 0 |
| 30 | 6.5 | 6.0 | 11.5 | 1.2 | 1.9 |
| 60 | 11.6 | 12.2 | 18.3 | 3.5 | 3.8 |
| 90 | 17.0 | 16.2 | 24.3 | 4.1 | 4.0 |
| 120 | 21.2 | 19.9 | 28.1 | 4.9 | 4.1 |

As described in detail above, because the catalyst particle of the present invention comprises an active metal and a carbon carrier, the active metal being supported by cavities formed on the carbon carrier surface and their edge portions, it can firmly support the active metal for a long period of time, thereby stably showing a high catalytic activity, which is hardly reduced by the reaction.

What is claimed is:

1. A catalyst particle comprising an active metal and a carrier composed of a carbon material, wherein said active metal is supported by cavities having an average diameter of 0.5 to 5 nm formed on a surface of said carrier and their edge portions, and wherein said carrier has an average particle size of 0.01 to 10 μm, wherein said carrier comprises a mesophase carbon composed of oriented crystallites comprising a basal plane having a cyclic structure and an edge having functional groups of —OH and —COOH.

2. The catalyst particle according to claim 1, wherein said carrier comprises at least one carbon material selected from the group consisting of cup-stacked-type carbon, carbon nanotubes, carbon nanofibers and carbon nanohorns.

3. The catalyst particle according to claim 1, wherein said carrier comprises an activated carbon having a surface area of 80 to 3000 $m^2/g$.

4. The catalyst particle according to claim 1, wherein said active metal comprises Ru, Pt or an alloy thereof.

5. A method for dehydrogenation of alcohol comprising contacting the catalyst particle according to claim 1 with an alcohol.

* * * * *